United States Patent [19]

Lichtenberger

[11] Patent Number: 4,598,705
[45] Date of Patent: Jul. 8, 1986

[54] TRACHEA CANNULA

[76] Inventor: György Lichtenberger, Pozsonyi út 15-17. V.1., H-1137 Budapest, Hungary

[21] Appl. No.: 662,406

[22] PCT Filed: Jan. 13, 1984

[86] PCT No.: PCT/HU84/00002
§ 371 Date: Sep. 14, 1984
§ 102(e) Date: Sep. 14, 1984

[87] PCT Pub. No.: WO84/02657
PCT Pub. Date: Jul. 19, 1984

[30] Foreign Application Priority Data

Jan. 14, 1983 [HU] Hungary .................................. 124/83

[51] Int. Cl.⁴ ............................................ A61M 16/00
[52] U.S. Cl. ............................ 128/200.26; 128/207.14
[58] Field of Search ................. 128/200.26, 207.14, 128/207.16, 207.17, 132 R, 205.29

[56] References Cited

U.S. PATENT DOCUMENTS

| 2,039,142 | 4/1936 | Brehar | 128/207.17 |
| 2,804,076 | 8/1957 | Giraudon | 128/207.16 |
| 3,088,466 | 5/1963 | Nichols | 128/200.26 |
| 3,334,631 | 8/1967 | Stebleton | 128/200.26 |
| 3,827,440 | 8/1974 | Birch et al. | 128/207.16 |

FOREIGN PATENT DOCUMENTS 810517  3/1959  United Kingdom ........... 128/207.14

Primary Examiner—Henry J. Recla
Attorney, Agent, or Firm—Handal & Morofsky

[57] ABSTRACT

According to the invention, an improved trachea cannula comprising a curved outer tube (2) and an inner tube (3) that is slidably and removably fitted within said outer tube (2) is provided for. The outer tube (2) is insertable into the trachea of a patient through a neck hole opened surgically by laryngotracheotomy in a manner known per se. The improvement consists in said trachea cannula being equipped with a box-like receptacle (1), preferably of the disposable kind made of plastic material, which is attached to the open outer end of said inner tube (3) by snap fastening for preventing uncontrolled discharge into the surroundings of the patient.

6 Claims, 4 Drawing Figures

TRACHEA CANNULA

TECHNICAL FIELD OF THE INVENTION

The present invention relates to an improved trachea cannula comprising a curved outer tube and an inner tube that is slidably and removably fitted within said outer tube. The outer tube is insertable into the trachea of a patient through a neck hole that is opened surgically by laryngotracheotomy in a manner known per se.

DESCRIPTION OF THE PRIOR ART

There are a large number of patients suffering from various kinds of throat troubles, such as laryngitis, cancer of the larynx etc. Many whose lives have been saved by surgical treatment, especially by a total removal of the larynx. Such people can survive the operation by 5 to 10 or even 20 years. However, as a result of said operation they are obliged to use a trachea cannula, a device as indicated briefly above, and through this they are put to great inconvenience. It is vital that they should use the trachea cannula, otherwise the neck hole made by laryngotracheotomy for breathing will narrow, and this may lead to suffocation.

The known prior art trachea cannulae used all over the world save the patients from suffocation. It is a disadvantage, however, that the outer end of the inner tube of such devices opens directly into the surroundings of the patient, and when they cough, secretion from the trachea is discharged into the ambient air, endangering the health of other people, and sometimes causing disgust in others. Because of the reflex-like, spontaneous and sudden nature of the coughing the patients are not able to cover the free opening of the cannula with their handkerchiefs in time. Especially soon after the operation, or in case of patients who had been suffering from chronic tracheal catarrh, the discharge of secretion may be extremely excessive, and this puts the patients and people in their surroundings to an increased inconvenience. Experience has shown that the quality of life of patients who have been cured from their basic throat disease by surgical treatment as described above, is poor. They often develop depression, and may exclude themselves from social contacts.

The object of the present invention is to provide an improved trachea cannula which, in addition to enabling the patient to breathe freely, prevents infectious, and sometimes disgusting secretion from being discharged into the ambient air.

BRIEF DESCRIPTION OF THE INVENTION

The above object is achieved by an improved trachea cannula of the type previously indicated, in which, according to the present invention, the improvement lies in said trachea cannula being equipped with a box-like receptacle having at least one breathing hole and being attached to the open outer end of said inner tube in order to prevent secretion discharge into the surroundings of the patient. In preferred embodiments of the improved trachea cannula according to the invention the box-like receptacle may be of the disposable kind made of a plastic material. It may have a closed front wall, bottom, top and side walls and a rear wall facing the patient's chest. At least one breathing hole is arranged in the rear wall, or in at least one of the side walls of the receptacle in the near proximity of a coupling hole for the open outer end of the inner tube. The coupling hole should be cut from the rear wall of the receptacle so as to match at least partially in shape and the dimensions of the open outer end branch of said inner tube.

With other embodiments, there are two breathing holes in the rear wall of the receptacle, arranged at both sides adjacent to the coupling hole in a manner that the breathing holes and the coupling hole form a single shaped opening within the rear wall of the receptacle.

It has turned out to be advantageous if the improved trachea cannula according to the invention has also fixing means for securely attaching the receptacle to the open end branch of the inner tube in such a manner that allows it to be releasable. In certain embodiments, both said outer and inner tube may have flanges at their open outer ends respectively. The fixing means is preferably designed and constructed as a snap fastener comprising an annular ball section of the flange of the inner tube that is to be inserted under slight pressure into a matching spherical socket within the flange of the outer tube. Thus the meeting edges of the opposite parts of the snap fastener are held together, and their joining is further secured by a wire spring. Thus, they clamp securely the wall partitions of the rear wall around the coupling hole of the receptacle. In addition to this, the receptacle can easily be detached and renewed.

It is strongly recommended to use disposable thin-wall receptacles made of plastic material. In order to prevent deformation of the receptacle's front wall during breathing-in, distance pins, at least a pair, may protrude from the flange of the inner tube towards the front wall of the receptacle.

With presently known mass-production techniques of plastic press moulding or vacuum forming, it has become possible and economical to provide preferred embodiments of the trachea cannula according to the invention in which the inner tube and the receptacle are designed and shaped as a single integral disposable component part made entirely of cheap plastic material available at low cost to the manufacturer.

As mentioned already soon after the operation, or in case of patients who had been suffering from chronic tracheal catarrh, the discharge of secretion may be extremely excessive. In such mainly transitory cases, preferred embodiments of the trachea cannula according to the present invention have proved to be very useful wherein there is a pipe of reduced diameter arranged within the inner tube, the pipe having an inlet branch in the proximity of the lower inner end of the inner tube, and the pipe end is outside the receptacle. The pipe end is suitable for being connected to a sucking device, preferably a secretion pump for dependably removing excess secretion from the patient's trachea. Finally, in a further preferred embodiment the improved trachea cannula may also be equipped with a pipe that extends into the receptacle and has an inlet branch arranged within a suitable distance above the bottom wall of the same. The pipe has it's pipe end outside the receptacle for conveniently attaching a sucking device, preferably a secretion pump thereto for a temporary and dependable discharge of the contents of said receptacle.

With all embodiments of the trachea cannula in accordance with the present invention, shape and dimension of the receptacle may show a large variety. Designs of prismatic shape, disc-like embodiments or even oval ones may equally be chosen. Different sizes of receptacles may be of particular advantage too, in accordance with prevailing criteria. However, it is of fundamental importance that the receptacle applied should be able to prevent uncontrolled discharge of secretion into the patient's surroundings.

BRIEF DESCRIPTION OF THE DRAWINGS

In the following, the present invention will be more particularly described by way of example only, through preferred embodiments with reference to the accompanying drawings wherein.

DESCRIPTION OF PREFERRED EMBODIMENTS OF THE INVENTION

Figure 1:
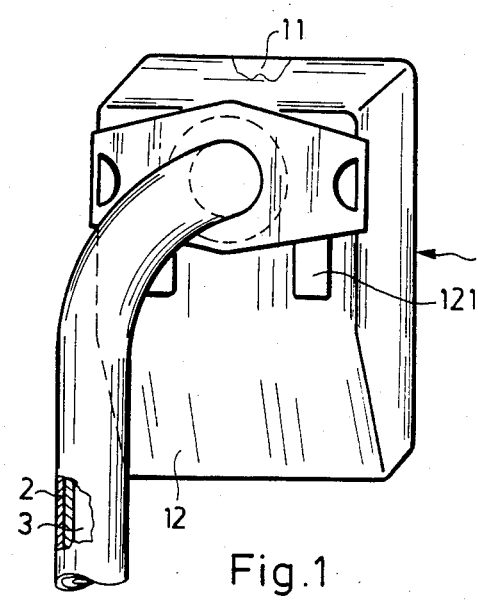
FIG. 1 shows a diagrammatic perspective view of a first preferred embodiment of an improved trachea cannula according to the present invention.
Figure 2:
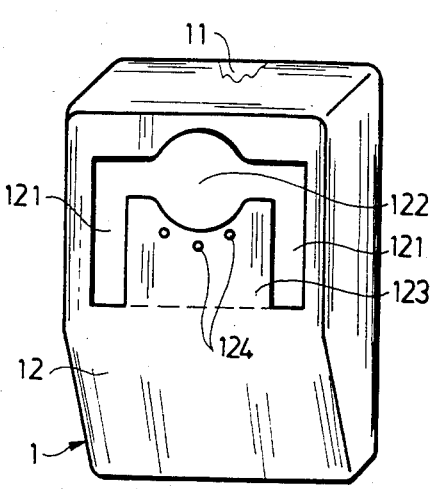
FIG. 2 shows the perspective view of the disposable receptacle of the embodiment indicated in FIG. 1, FIG. 3 indicates a cross-sectional longitudinal view of the embodiment according to FIG. 1 wherein details of a preferred fixing means are more clearly shown in a somewhat enlarged scale.
Figure 3:
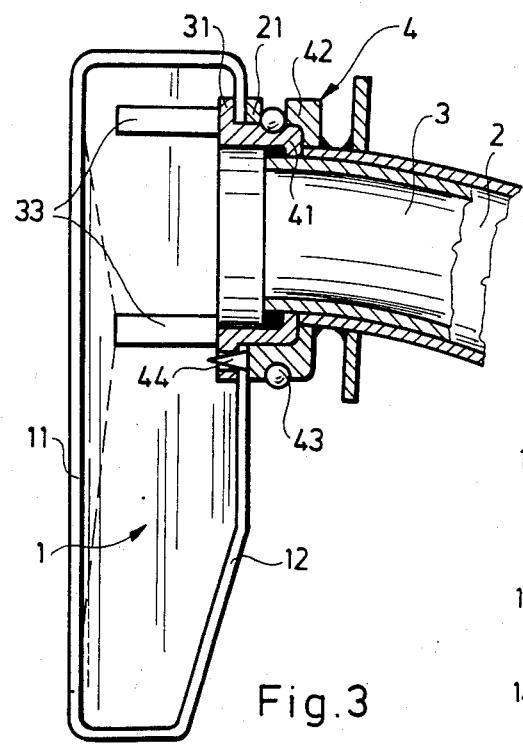

A first preferred embodiment of an improved trachea cannula according to the present invention is shown in FIG. 1 of the attached drawing. It comprises a curved outer tube 2 and an inner tube 3 that is slidable and fitted within and allowing for its removal from the outer tube 2. The latter is to be inserted into the trachea of the patient through a neck hole that had been opened by laryngotracheotomy, a surgical operation known per se. To the open outer end of the inner tube 3 a box-like receptacle 1 made of plastic material is attached in order to prevent secretion discharge into the surroundings of the patient. As mentioned already, the box-like receptacle 1 is of the disposable kind, and has a closed front wall 11, a rear wall 12 facing the patient's chest, bottom, top and side walls. FIG. 2 shows more clearly that the receptacle 1 further has two breathing holes 121 and a coupling hole 122 for the open outer end of the inner tube 3. The coupling hole 122 is cut out from the rear wall 12 of the receptacle 1 so as to match both in shape and dimension with the open outer end branch of the inner tube 3. More particularly, with the present embodiment as shown in FIGS. 1 and 2, the two breathing holes 121 in the rear wall 12 of the receptacle 1 are arranged at both sides close to the coupling hole 122 in a manner that the breathing holes 121 and the coupling hole 122 form a single, suitably shaped opening within the rear wall 12. Thus, between the breathing holes 121 there is a wall partition 123 provided for, and a flange 31, enabling somewhat enlarged diameter of the inner tube 3 to be inserted into the receptacle 1 by slight temporary deformation of said wall partition 123 along an elongated area of the latter as indicated by dotted line in FIG. 2. Upon inserting the inner tube 3 into the outer tube 2, the upper and lower rear wall areas around the coupling hole 122 are clamped and held between flanges 31 and 21 of the inner tube 3 and the outer tube 2 respectively, as it may be clearly seen in FIG. 3. Exact positioning of the receptacle 1 with respect to the tubes 2 and 3 is effected by locating pins 44 that protrude from the flange 21 of the outer tube 2, and correspond with locating bores 124 in the wall partition 123 of the rear wall 12 shown in FIG. 2. The flange 31 of the inner tube 3 has protruding distance pins 33 embedded into its periphery. They extend into the interior of the receptacle 1 towards its front wall 11, and preventing possible excess deformation of the latter during breathing-in (as indicated in FIG. 3 by thin dotted line) which could cause a narrowing of the cross-sectional air flow area, and thus, would make breathing more difficult.

The improved trachea cannula according to the present invention has also a fixing means 4 for securely but releasably attaching the receptacle 1 to the open end branch of the inner tube 3. Said fixing means may be preferably, though not exclusively, a snap fastener in principle, for which a preferred embodiment is clearly shown in FIG. 3. As already mentioned above, both the outer tube 2 and the inner tube 3 have flanges 21 and 31 respectively at their open outer ends. The fixing means 4, designed and shaped as a snap fastener for example only, comprises an annular wall section 41 of the flange 31, and it is insertable under slight pressure (against the tight fit and the action of a ring-shaped wire spring 43) into a matching spherical socket 42 within the flange 21.

Figure 4:
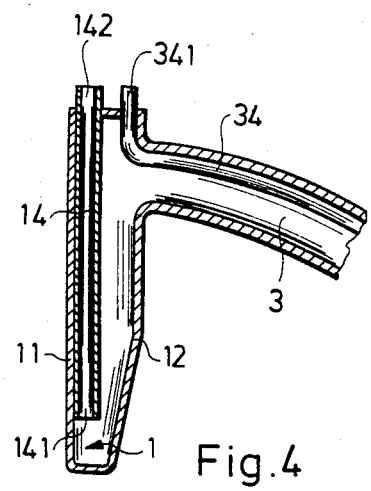
FIG. 4 shows the same cross-sectional longitudinal view of a further embodiment of the trachea cannula according to the invention where the inner tube and the receptacle are formed as a single disposable component part made entirely of plastic material.

As the main component part of a further preferred embodiment of the improved trachea cannula according to the present invention, FIG. 4 shows clearly that the inner tube 3 and the receptacle 1 may also be designed and shaped as a single integral disposable component part made of plastic material. In addition to this, FIG. 4 indicates that with certain preferred embodiments, a pipe 34 of reduced diameter can be arranged within the inner tube 3. The pipe 34 has an inlet branch (not shown) that is in the proximity of the inner lower end of the inner pipe 3, and a pipe end 341 outside the receptacle 1. The pipe end 341 is suitable for being connected to a sucking device (not shown), preferably to a secretion pump for dependably removing excess secretion from the patient's trachea, especially during the initial period soon after the operation. All embodiments of the device according to the present invention may have another pipe 14 extending into the receptacle 1. The pipe 14 has an inlet branch 142 that is arranged in a suitable distance above the bottom wall of the receptacle. To a pipe end 142 outside of the receptacle 1 a sucking device (not shown), preferably a secretion pump may be attached for temporary and dependable discharge of the contents of the receptacle 1 without removing the latter from its working position.

I claim:

1. An improved trachea cannula comprising a curved outer tube (2) and an inner tube (3) that is slidably and removably fitted within said outer tube (2), said outer tube (2) being insertable into the trachea of a patient through a neck hole opened surgically by laryngotracheotomy, wherein said trachea cannula comprises a box-like receptacle (1) having a coupling hole (122) attached to the open outer end of said inner tube (3) in order to prevent secretion discharge into the surroundings of the patient, wherein said box-like receptacle (1) is of the disposable kind made preferably of plastic material, and having a closed front wall (11) a rear wall (12) facing the patient's chest, bottom, top and side walls, said coupling hole (122) being cut out from the rear wall (12) of said receptacle (1) so as to match both in shape and dimension at least partially the open outer end branch of said inner tube (3), comprising two breathing holes (121) in the rear wall (12) of said receptacle (1), arranged at both sides close to said coupling hole (122) for the open outer end of said inner tube (3)

in a manner that said breathing holes (121) and the coupling hole (122) form a single shaped opening within said rear wall (12) of said receptacle (1).

2. An improved trachea cannula as claimed in claim 1 characterized in having a fixing means (4) for securely but releasably attaching said receptacle (1) to the open outer end branch of said inner tube (3).

3. An improved trachea cannula as claimed in claim 1 characterized in both said outer and inner tube (2,3) having flanges (21,31) at their open outer ends respectively, and said fixing means (4) being designed and constructed as a snap fastener comprising an annular wall section (41) of said flange (31) of the inner tube (3), said annular wall section being insertable under slight pressure into a matching spherical socket (42) within said flange (21) of the outer tube (2), and said flanges (21,31) clamping securely wall partitions of the rear wall (12) of said receptacle (1).

4. An improved trachea cannula comprising a curved outer tube (2) and an inner tube (3) that is slidably and removably fitted within said outer tube (2), said inner tube having an open outer end with a peripheral flange (31) extending therefrom, said outer tube (2) being insertable into the trachea of a patient through a neck hole opened surgically by laryngotracheotomy, wherein said trachea cannula comprises a box-like receptacle (1) having at least one breathing hole (121), a coupling hole (122) mounted over said flange (31) on the open outer end of said inner tube (3) in order to prevent secretion discharge into the surroundings of the patient, wherein said box-like receptacle (1) is of the disposable kind made preferably of plastic material, and having a closed front wall (11) a rear wall (12) facing the patient's chest, bottom, top and side walls, said receptacle (1) said breathing hole (121) being arranged in said rear wall (12) in the near proximity of a coupling hole (122) for said open outer end of the inner tube (3), and said coupling hole (122) being cut out from the rear wall (12) of said receptacle (1) so as to match both in shape and dimension at least partially the open outer end branch of said inner tube (3), further comprising at least a pair of distance pins (33) protruding from said flange (31) of said inner tube (3) towards the front wall (11) of said receptable (1).

5. An improved trachea cannula comprising a curved outer tube (2) and an inner tube (3) that is slidably and removably fitted within said outer tube (2), said outer tube (2) being insertable into the trachea of a patient through a neck hole opened surgically by laryngotracheotomy, wherein said trachea cannula comprises a box-like receptacle (1) having at least one breathing hole (121), a coupling hole (122) attached to the open outer end of said inner tube (3) in order to prevent secretion discharge into the surroundings of the patient, further comprising a pipe (34) of reduced diameter arranged within said inner tube (3), said pipe (34) having an inlet branch in the proximity of the inner lower end of said inner tube (3), and a pipe end (341) outside said receptacle (1), said pipe end (341) being suitable for being connected to a sucking device, preferably a secretion pump for positively removing excess secretion from the patient's trachea.

6. An improved trachea cannula comprising a curved outer tube (2) and an inner tube (3) that is slidably and removably fitted within said outer tube (2), said outer tube (2) being insertable into the trachea of a patient through a neck hole opened surgically by laryngotracheotomy, wherein said trachea cannula comprises a box-like receptacle (1) having at least one breathing hole (121), a coupling hole (122) attached to the open outer end of said inner tube (3) in order to prevent secretion discharge into the surroundings of the patient, further comprising a pipe (14) extending into said receptacle (1), said pipe (14) having an inlet branch (142) that is arranged within a suitable distance above the bottom wall of the receptacle (1), and said pipe having a pipe end (141) outside of said receptacle (1) for attaching a sucking device, preferably a secretion pump thereto for a temporary and positive discharge of the contents of said receptable (1).

* * * * *